US009119977B2

(12) United States Patent
Rittner et al.

(10) Patent No.: US 9,119,977 B2
(45) Date of Patent: Sep. 1, 2015

(54) OXYGEN BREATHING DEVICE WITH MASS FLOW CONTROL

(75) Inventors: Wolfgang Rittner, Siblin (DE); Rudiger Meckes, Berkenthin (DE); Gunter Boomgarden, Scharbeutz (DE)

(73) Assignee: Zodiac Aerotechnics, Plaisir (FR)

( * ) Notice: Subject to any disclaimer, the term of this patent is extended or adjusted under 35 U.S.C. 154(b) by 625 days.

(21) Appl. No.: 12/501,513

(22) Filed: Jul. 13, 2009

(65) Prior Publication Data

US 2010/0012123 A1 Jan. 21, 2010

Related U.S. Application Data

(60) Provisional application No. 61/079,830, filed on Jul. 11, 2008.

(51) Int. Cl.
*A62B 7/00* (2006.01)
*A62B 7/14* (2006.01)
*A61M 16/00* (2006.01)
*F16K 31/02* (2006.01)

(52) U.S. Cl.
CPC ........................................ *A62B 7/14* (2013.01)

(58) Field of Classification Search
USPC ............. 128/202.12, 204.18, 205.11–205.12, 128/205.24, 205.26–205.28
See application file for complete search history.

(56) References Cited

U.S. PATENT DOCUMENTS

| | | | | |
|---|---|---|---|---|
| 4,651,728 | A * | 3/1987 | Gupta et al. | 128/201.28 |
| 4,823,788 | A * | 4/1989 | Smith et al. | 128/205.24 |
| 5,809,999 | A * | 9/1998 | Lang | 128/200.24 |
| 6,155,258 | A * | 12/2000 | Voege | 128/205.21 |
| 6,962,154 | B2 * | 11/2005 | Krebs | 128/203.12 |
| 6,986,351 | B2 * | 1/2006 | Figley et al. | 128/205.24 |
| 7,100,800 | B2 * | 9/2006 | Yakasovic Saavedra et al. | 222/3 |
| 7,861,717 | B1 * | 1/2011 | Krebs | 128/204.23 |
| 2004/0000312 | A1 * | 1/2004 | Matheny et al. | 128/205.22 |
| 2004/0171983 | A1 * | 9/2004 | Sparks et al. | 604/65 |
| 2004/0244585 | A1 | 12/2004 | Meckes et al. | |
| 2005/0247311 | A1 * | 11/2005 | Vacchiano et al. | 128/203.12 |
| 2007/0151333 | A1 * | 7/2007 | Paradise | 73/118.1 |
| 2008/0078338 | A1 * | 4/2008 | Meintschel et al. | 123/3 |
| 2008/0318172 | A1 * | 12/2008 | Geiger et al. | 431/12 |
| 2009/0013996 | A1 * | 1/2009 | Rittner et al. | 128/202.22 |
| 2009/0081804 | A1 * | 3/2009 | Tuchman | 436/158 |

FOREIGN PATENT DOCUMENTS

| | | | |
|---|---|---|---|
| WO | WO 03033076 | A1 * | 4/2003 |
| WO | WO 2006005372 | | 1/2006 |

* cited by examiner

*Primary Examiner* — Tan-Uyen (Jackie) T Ho
*Assistant Examiner* — Mark Wardas
(74) *Attorney, Agent, or Firm* — Kilpatrick Townsend & Stockton LLP; Dean W. Russell, Esq.; Kristin M. Crall, Esq.

(57) ABSTRACT

The present invention relates to an oxygen breathing device, in particular for providing oxygen to passengers or crew of an aircraft, the device comprising an oxygen source for providing pressurized oxygen, a valve connected to the oxygen source via a pressure line, a control unit for controlling said valve, and at least one nozzle for dispensing the oxygen passing through said valve. In particular, the present invention relates to an oxygen breathing device comprising a measuring unit for determining the mass flow rate of oxygen passing through said nozzle. Furthermore, the invention relates to a method for supplying oxygen to a person, in particular a flight passenger, using an oxygen breathing device.

10 Claims, 1 Drawing Sheet

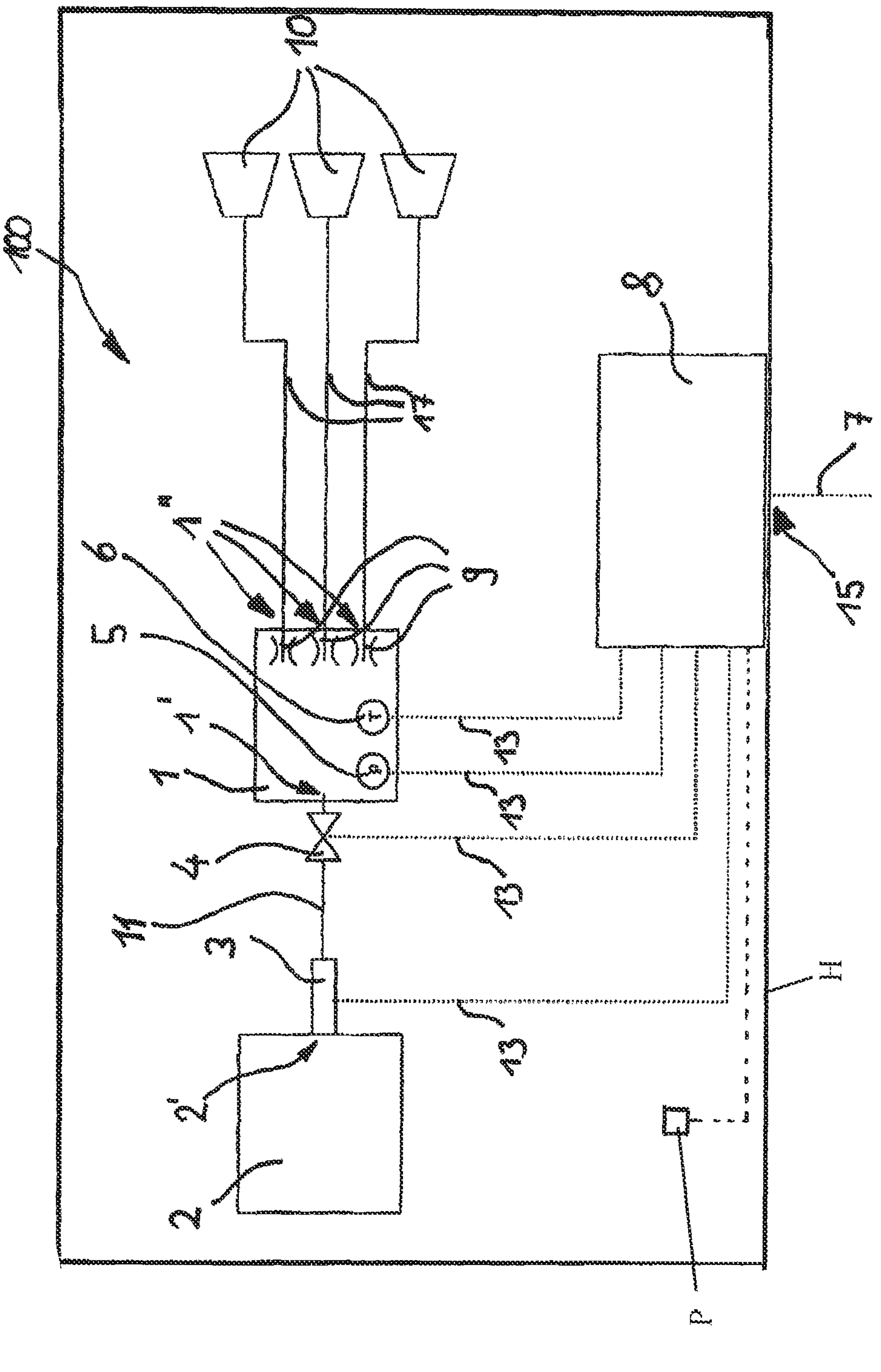
100
10
8
7
15
6
5
9
4
3
2
13
H
P

OXYGEN BREATHING DEVICE WITH MASS FLOW CONTROL

CROSS REFERENCE TO RELATED APPLICATION

This application claims the benefit of U.S. Provisional Application No. 61/079,830 filed on Jul. 11, 2008, the entire contents of which are incorporated herein by reference.

BACKGROUND

This invention relates to an oxygen breathing device, in particular for providing oxygen to passengers or crew of an aircraft, the device comprising an oxygen source for providing pressurized oxygen, a valve connected to the oxygen source via a pressure line, a control unit for controlling said valve, and at least one nozzle for dispensing the oxygen passing through said valve.

Furthermore, the invention relates to a method for supplying oxygen to a person, in particular a flight passenger, using an oxygen breathing device.

FIELD OF THE INVENTION

Oxygen breathing devices of the aforementioned construction are used for a number of purposes where temporary or permanent supply of oxygen to a human person is necessary. A particular field of application of such oxygen breathing devices is the field of aircraft, wherein a pressure drop within an aircraft flying at high altitude may make it necessary to supply the passengers and the crew members with oxygen to ensure sufficient oxygen supply to these persons. Usually, an oxygen breathing device is provided for each crew member and passenger or a group thereof and is usually arranged above the passenger. In case of an emergency, such oxygen breathing device is activated, for example automatically by a cabin pressure monitoring system or manually by a crew member, whereafter an oxygen mask connected via a hose to an oxygen source falls from above the passenger downwards and can be used by the passenger. The flow of oxygen may be started automatically by activation of the system by the crew member or may be activated by a particular action undertaken by the passenger, e.g. by pulling the mask towards himself to thus activate the device by a pulling force transferred via the hose guiding the oxygen flow or an additional lanyard coupled to the oxygen mask.

For oxygen-supplying systems on board of aircrafts, oxygen flow rates are defined in the aviation standards depending upon aircraft altitude. In order to develop a system for supplying passengers with oxygen which is highly efficient, this system has to be designed to include means for controlling oxygen flow rate as a function of altitude air pressure or as a function of a time schedule in accordance with an aircraft descent profile.

State of the art oxygen controllers are designed as pressure controllers which control the pressure of an outlet nozzle as a function of ambient pressure. A primary pressure upstream of the nozzle is produced such that a supercritical pressure ratio appears across the nozzle, over a wide range of operating conditions. The flow rate resulting herefrom maintains a linear relation with the inlet pressure as long as the temperature upstream of the nozzle is constant. Under real life conditions, this is not the case however.

Due to typically occurring variations of ambient temperature as well as due to system cooling resulting from the Joule-Thompson effect, flow rates vary by about 20%. As a consequence hereof, more oxygen has to be transported by the aircraft which results in higher system weight having to be built into the aircraft. Inherent drawbacks of these known systems are higher fuel consumption, higher construction and design costs and lacking precision in oxygen supply.

SUMMARY OF THE INVENTION

It is thus an object of the present invention to provide an oxygen breathing device with improved flow control performance.

This object is fulfilled by providing an oxygen breathing device as described in the introductory portion, comprising a measuring unit for determining the mass flow rate of oxygen passing through said nozzle.

According to a first aspect of the invention, a measuring unit is integrated into the oxygen breathing device. The measuring unit provides information which makes it possible to directly determine the mass flow rate of oxygen passing through the nozzle. The information gathered by the measuring unit can advantageously be used in controlling the breathing device's oxygen throughput, thus limiting the amount of oxygen dispensed through the nozzle. Since the exact amount of oxygen needed can now be determined, there is no longer any need storing and/or dispensing surplus amount of quantities of oxygen as a precautionary measure. Furthermore, the mass flow rate of oxygen can be controlled precisely since the measuring unit can instantly provide a feedback of how valve control affects the mass flow throughput.

According to a preferred embodiment of the invention, the measuring unit comprises a temperature sensor for measuring the temperature of oxygen passing through said nozzle and a pressure sensor for measuring the pressure of oxygen passing through said nozzle. Whereas the operation of known oxygen breathing systems was based on an estimation of flow rate as a function of a primary pressure upstream of the nozzle and the assumption of a supercritical pressure regime across the nozzle, the oxygen breathing device according to the present invention enables controlling the mass flow rate directly as a function of pressure and temperature. By integrating a temperature sensor in addition to a pressure sensor, it becomes possible to determine the mass flow rate of oxygen passing through the nozzle and at the same time to take into account any changes in temperature that may occur during flight and/or operation of the oxygen breathing device.

According to a further preferred embodiment of the invention, the pressure sensor and the temperature sensor are located inside a measurement chamber comprising an inlet and at least one outlet, wherein said nozzle is associated with said outlet and the inlet is connected to the oxygen source in a fluid-conducting manner. The measurement chamber is advantageously designed to be gas-tight such that no oxygen or other fluid can enter and/or exit the measurement chamber except through the inlet or outlet of said chamber. Specific operating conditions may require the inlet and the outlet to be sealed against their respective counterparts to further improve the tightness of the measurement chamber. By providing a gas-tight measurement chamber, the pressure sensor and temperature sensor are able to provide measurement information which is independent of exterior influences. Both the pressure sensor and the temperature sensor may be installed inside the measurement chamber in such way that they do not significantly interfere with the conduit along which oxygen is passed through the measurement chamber to the nozzle. Such layout contributes to minimizing flow losses.

According to another preferred embodiment of the present invention, the control unit is adapted to calculating the mass flow rate of oxygen passing through the measurement chamber and/or the nozzle, and comprises a data storage unit adapted for writing calibration parameters to and reading said calibration parameters from said data storage unit. The control unit is connected to the temperature sensor and the pressure sensor of the measuring unit in a wired or wireless manner and adapted to receiving temperature-representative signals from the temperature sensor and/or pressure-representative signals from the pressure sensor. Based upon this information and upon information received from the data storage unit the control unit is able to calculate the mass flow rate of oxygen passing through the measurement chamber. This information can be used by the control unit itself to manipulate the valve to increase or decrease its conduit so as to adjust the mass flow rate of oxygen. Furthermore, the control unit is connected to the data storage unit for storing calibration data and/or for reading calibration data from the storage unit in order to adapt to different operating conditions. Thus, the oxygen breathing device is adapted to provide the correct mass flow rate of oxygen in various situations with differing operating conditions.

The data storage unit may be any type of physical storage medium, such as a hard disk drive, flash memory or optical media.

According to another preferred embodiment of the present invention, the control unit is selectively operable in a time-controlled and/or ambient pressure-controlled manner. The amount of oxygen required by persons using the oxygen breathing system largely depends on the altitude of the aircraft. Accordingly, changing altitude requires a matching change of mass flow of the oxygen breathing device. Such change can be taken into account by the control unit on the one hand by monitoring the ambient pressure and including this information into the calculation process. On the other hand, where ambient pressure information is not available or where it is not desired to include this information, the control unit can be operated based upon a timing schedule. Such a schedule should be congruent with the descent profile of the aircraft. A steeper descent results in a faster change of the required quantity of oxygen.

According another preferred embodiment of the present invention, the oxygen breathing device further comprises at least one breathing mask for supplying oxygen to a person, which is connected to said nozzle via a fluid pipe.

In accordance with another preferred embodiment of the present invention, the oxygen breathing device further comprises an ambient pressure sensor, shown as reference "P" in FIG. 1, adapted for transmitting pressure signals to the control unit. Depending on the specific design of an oxygen breathing device according to the invention such ambient pressure sensor may be integrated into a common housing of the breathing device, indicated as reference "H" in FIG. 1, or may also be installed separately in a suitable location of the aircraft. Advantageously, the ambient pressure sensor is connected to the control unit via a wired or wireless connection. Optionally, the ambient pressure sensor may also be connected to the control unit via a supply line which provides external signal information and/or electric energy to the control unit.

According to another preferred embodiment of the present invention, the valve is designed as an electro-pneumatic control valve, in particular as a proportional solenoid valve, on/off magnet valve or motor-driven servo valve. Electro-pneumatic valves such as the aforementioned types allow for precise conduit control while at the same time being highly reactive to control signals. Using such types of valves hence enables precise and fast mass flow control. It is understood that other types of valves featuring similar characteristics may also be employed.

According to another preferred embodiment of the oxygen breathing device according to the invention, the oxygen breathing device further comprises a starting unit for releasing pressurized oxygen from the oxygen source to said pressure line, said starting unit comprising a closing member adapted to closing or opening the pressure line.

This embodiment can further be improved in that the starting unit is electrically actuable via the control unit if a pressure drop is detected by the ambient pressure sensor. Designing the starting unit to be electrically actuable is particularly advantageous since the operation of the oxygen breathing device according to the present invention can be initiated very quickly through the control unit. In order to accomplish this, an electrical signal is transmitted from the control unit to the starting unit if certain starting conditions are met. A sufficiently strong pressure drop inside the aircraft or in particular inside the passenger cabin is considered to be an adequate and measurable starting condition in this respect.

According to a further preferred embodiment of the invention, the starting unit is mechanically actuable via actuation means.

This embodiment can be further improved in that the actuation means comprise a release pin removably attached to the closing member such that the closing member is locked in a closing state, and pulling means connected to said release pin, wherein said pulling means are generally moveable to detach the release pin from the closing member. Such a mechanical system for initiating the operation of the oxygen breathing device according to the invention is considered as advantageous in the light of possible functions of the control unit. If for whatever reasons the control unit fails to transmit a starting signal to the starting unit, oxygen supply may still be initiated mechanically. Unlocking the closing member by removing a release pin mechanically is a simple, reliable and cost-effective way of achieving this.

According to a further improved embodiment of the present invention, the pulling means are designed as a pull cord and connected to the breathing mask such that the pull cord is tensible by moving the breathing mask towards a user. The user, in particular a flight passenger, can thus initiate oxygen supply to the mask associated with his seating position inside the aircraft autonomously and does not have to wait for the system to enable said oxygen supply.

According to a second aspect of the invention, a method for supplying oxygen to a person, in particular a flight passenger, using an oxygen breathing device is provided the method comprising the steps of providing pressurized oxygen to a pressure line from an oxygen source, controlling the flow of oxygen through a valve connected to the oxygen source through the pressure line, via a control unit, streaming pressurized oxygen from the oxygen source to a nozzle through said pressure line, passing said oxygen through said nozzle, and determining the mass flow rate of said oxygen via a measuring unit. The method may in particular be accomplished using an oxygen breathing device as described above.

In a further embodiment of the method according to this invention, said method further comprises the steps of streaming said pressurized oxygen through a measurement chamber, transmitting a pressure signal from a pressure sensor to the control unit, transmitting a temperature signal from a temperature sensor to the control unit, transmitting an ambient pressure signal from an ambient pressure sensor to the control unit, calculating the oxygen mass flow rate via the control unit, reading a setpoint mass flow value from a data storage unit, comparing said setpoint mass flow value to said actual mass flow rate, and adjusting the mass flow rate to equal the setpoint mass flow value. The data stored on the data storage unit is preferably allocated in look-up tables. However, it is understood that alternative ways of data organization will readily appear to those skilled in the art.

According to a further preferred embodiment of the method according to this invention, the method further comprises a calibration process, said calibration process comprising the steps of determining system and ambience parameters via the nozzle, writing the system and ambience parameters to the data storage unit, and allocating setpoint mass flow values to said parameters. Said calibration process is achieved with highly precise nozzles for each outlet. These nozzles ensure that under the given conditions inside the measuring chamber, the mass flow rates through the nozzles are reproducible within narrow ranges of tolerance. The system is calibrated with varying system and ambience parameters such as ambient pressure, to meet certain oxygen mass flow rates through the nozzles, and the measuring and system parameters obtained herein—including the ambient pressures—are stored in look-up tables in the data storage unit.

According to a further preferred embodiment of the method according to the invention, the mass flow rate is controlled via the control unit as a function of a time schedule stored in the data storage unit.

According to a further preferred embodiment of the method according to the invention, the mass flow rate is controlled via the control unit as a function of the ambient pressure.

A preferred embodiment of the invention will be described hereinafter with reference to the accompanying figure, wherein the figure is a schematical view of an oxygen breathing system according to a preferred embodiment of the invention.

BRIEF DESCRIPTION OF THE DRAWING

With reference to FIG. 1, an oxygen breathing system 100 is illustrated. Pressurized oxygen is stored inside an oxygen source 2. The oxygen source 2 comprises an outlet 2'. A starting unit 3 is connected to said outlet 2'. Furthermore, the starting unit 3 is associated with a pressure line 11, which is adapted to interconnect the oxygen source 2 and a valve 4. Valve 4 in the depicted embodiment is an electro-pneumatic control valve. A valve 4 is associated with an inlet 1' of a measurement chamber 1.

DETAILED DESCRIPTION

The measurement chamber comprises three outlets 1" which are each associated with a nozzle 9. The nozzles 9 are each adapted to dispense oxygen into fluid lines 17 each of which are connected to a breathing mask 10. The breathing masks 10 are adapted to be pressed against a passenger's face in order to supply oxygen to the passenger's respiratory tract.

The oxygen breathing device 100 of the figure further comprises an electronic control unit 8. The control unit 8 is connected to the starting unit 3, to the valve 4, to a pressure sensor 5 and to a temperature sensor 6, respectively, via electric cables 13. The pressure sensor 5 and the temperature sensor 6 are located inside the measurement chamber 1. The pressure sensor 5 of the depicted embodiment is a total pressure sensor. Both the pressure sensor 5 and the temperature sensor 6 are located inside the measurement chamber in order to measure the pressure and temperature, respectively, inside the measurement chamber and in order to provide signal information to the control unit 8. The control unit 8 furthermore comprises a port 15 with an aircraft-sided supply line for supplying electric energy and/or signals are connected to supply line 7.

In case of a loss of pressure inside the aircraft, the aircraft-sided energy supply is activated. An electric signal is transmitted to the electronic control unit 8. The electronic control unit 8 then transmits a signal to the starting unit 3, and subsequently, the oxygen source 2 releases pressurized oxygen through the pressure line 11 to the electro-pneumatic valve 4.

From the outlet of the electro-pneumatic valve 4, the oxygen is passed directly into the measurement chamber 1. Inside the measurement chamber 1, the total pressure sensor 5 and the temperature sensor 6 measure the pressure and temperature inside the measurement chamber. These measurands are transmitted to the electronic control unit 8 in the form of electric signals. The control unit 8 controls the electro-pneumatic control valve 4 as a function of these two measurands and either the ambient pressure and/or a time value. With the help of a look-up table (not shown), a total pressure can be adjusted inside the measurement chamber as a function of the temperature inside the measurement chamber which results in a specific mass flow rate being realized through each individual nozzle 9 and being guided to the breathing masks 10.

While reference has been made to oxygen in this specification, it is understood that the term oxygen is used synonymically for any gas mixture containing oxygen which qualifies for being supplied to a human being for health and/or life support.

Whereas the invention has been described with reference to a preferred embodiment, it is to be understood that the description and the figure is to be understood as a descriptive but not limiting example.

The invention claimed is:

1. An oxygen breathing device for providing oxygen to passengers or crew of an aircraft, the device comprising:

an oxygen source for providing pressurized oxygen, a valve connected to the oxygen source via a pressure line, a control unit for controlling said valve, at least one nozzle for dispensing the oxygen passing through said valve, a common housing and an ambient pressure sensor integrated into the common housing of the breathing device and being adapted for transmitting pressure signals to the control unit, a measuring chamber having a housing adapted for use within a cabin of the aircraft for determining the mass flow rate of oxygen passing through said nozzle, the measuring chamber comprising an inlet and at least one outlet, the inlet connected to the oxygen source in a fluid-conducting manner;

at least one nozzle associated with the outlet for dispensing oxygen;

a temperature sensor for measuring the temperature of oxygen passing through said nozzle, and a second pressure sensor for measuring the pressure of oxygen passing through said nozzle, wherein the second pressure sensor and the temperature sensor are located inside the housing of the measurement chamber;

the control unit being connected to the temperature sensor and the second pressure sensor of the measurement chamber in a wired or wireless manner and adapted to receive temperature-representative signals from the temperature sensor, pressure-representative signals from the pressure sensor, or both, and wherein the control unit is adapted to calculate the mass flow rate of oxygen passing through the measurement chamber and comprises a data storage unit adapted for writing calibration parameters to and reading said calibration parameters from said data storage unit;

and a starting unit for releasing the pressurized oxygen from the oxygen source to the pressure line, wherein the starting unit is electrically actuated via the control unit if a passenger cabin drop is detected by the ambient pressure sensor.

2. The oxygen breathing device of claim 1, wherein the control unit is selectively operable in a time-controlled and/or ambient pressure-controlled manner.

3. The oxygen breathing device of claim 1, wherein the valve is designed as an electro-pneumatic control valve selected from the group consisting of a proportional solenoid valve, an on/off magnet valve or a motor-driven servo valve.

4. The oxygen breathing device of claim 1, further comprising more than one breathing mask for supplying oxygen to a passenger.

5. An oxygen breathing device for providing oxygen to passengers or crew of an aircraft, the device comprising:

an oxygen source for providing pressurized oxygen, a valve connected to the oxygen source via a pressure line, a control unit for controlling said valve, at least one nozzle for dispensing the oxygen passing through said valve, a common housing and an ambient pressure sensor integrated into the common housing of the breathing device and being adapted for transmitting pressure signals to the control unit, a measuring chamber having a housing adapted for use within a cabin of the aircraft for determining the mass flow rate of oxygen passing through said nozzle, the measuring chamber comprising an inlet and at least one outlet, the inlet connected to the oxygen source in a fluid-conducting manner;

at least one nozzle associated with the outlet for dispensing oxygen;

a temperature sensor for measuring the temperature of oxygen passing through said nozzle, and a second pressure sensor for measuring the pressure of oxygen passing through said nozzle, wherein the second pressure sensor and the temperature sensor are located inside the housing of the measurement chamber;

the control unit being connected to the temperature sensor and the second pressure sensor of the measurement chamber in a wired or wireless manner and adapted to receive temperature-representative signals from the temperature sensor, pressure-representative signals from the pressure sensor, or both, and wherein the control unit is adapted to calculate the mass flow rate of oxygen passing through the measurement chamber and comprises a data storage unit adapted for writing calibration parameters to and reading said calibration parameters from said data storage unit;

a starting unit for releasing the pressurized oxygen from the oxygen source to the pressure line, the starting unit comprising a closing member adapted to close or open the pressure line; and an actuation means for mechanically actuating the starting unit, the actuation means comprising (i) a release pin removably attached to the closing member such that the closing member is locked in a closing state and (ii) a pulling means connected to the release pin, wherein the pulling means are moveable to detach the release pin from the closing member.

6. The oxygen breathing device of claim 5, wherein the valve is designed as an electro-pneumatic control valve selected from the group consisting of a proportional solenoid valve, an on/off magnet valve or a motor-driven servo valve.

7. The oxygen breathing device of claim 5, wherein the control unit is adapted to calculate the mass flow rate of oxygen passing through the measurement chamber and comprises a data storage unit adapted for writing calibration parameters to and reading said calibration parameters from said data storage unit.

8. The oxygen breathing device of claim 5, further comprising more than one breathing mask for supplying oxygen to a passenger.

9. An oxygen breathing device for providing oxygen to passengers or crew of an aircraft, the device comprising:

an oxygen source for providing pressurized oxygen, the oxygen source comprising an outlet, a valve connected to the oxygen source via a pressure line, a starting unit which is connected said outlet of said oxygen source;

at least one nozzle for dispensing the oxygen passing through said valve; a measuring unit for determining the mass flow rate of oxygen passing through said nozzle, the measuring unit comprising a housing having an inlet and an outlet, and said valve being associated with the inlet and said nozzle being associated with the outlet, wherein the at least one nozzle is adapted to dispense oxygen into a fluid line which is connected to a breathing mask being adapted to be pressed against a passenger's face in order to supply oxygen to the passenger's respiratory tract;

a control unit for controlling said valve and said starting unit, said control unit being connected to the starting unit via the valve, to a pressure sensor and to a temperature sensor, respectively, via electric cables, wherein the pressure sensor and the temperature sensor are located inside said measuring unit to measure the pressure and temperature, respectively, inside the measuring unit and to provide signal information to the control unit;

the control unit further comprising a port with an aircraft-sided supply line for supplying electric energy and/or signals;

wherein the control unit transmits, upon receiving a corresponding signal from the aircraft-sided supply, a signal to the starting unit, and subsequently, the oxygen source releases pressurized oxygen through said pressure line to said valve, wherein oxygen is passed directly into the inlet of the measuring unit, inside which the pressure sensor and the temperature sensor measure the pressure and temperature inside the housing of the measuring unit, wherein these measurements are transmitted to the control unit in the form of electric signals and the control unit controls the valve as a function of the pressure and temperature inside the measuring unit and either the ambient pressure and/or a time value.

10. An oxygen breathing device for providing oxygen to passengers or crew of an aircraft, the device comprising:

an oxygen source for providing pressurized oxygen, a valve connected to the oxygen source via a pressure line, a control unit for controlling said valve, at least one nozzle for dispensing the oxygen passing through said valve, a common housing and an ambient pressure sensor integrated into the common housing of the breathing device and being adapted for transmitting pressure signals to the control unit, a measuring chamber having a housing adapted for use within a cabin of the aircraft for determining the mass flow rate of oxygen passing through said nozzle, the measuring chamber comprising an inlet and at least one outlet, the inlet connected to the oxygen source in a fluid-conducting manner;

at least one nozzle associated with the outlet for dispensing oxygen;

a temperature sensor for measuring the temperature of oxygen passing through said nozzle, and a second pressure sensor for measuring the pressure of oxygen passing through said nozzle, wherein the second pressure sensor and the temperature sensor are located inside the housing of the measurement chamber;

the control unit being connected to the temperature sensor and the second pressure sensor of the measurement chamber in a wired or wireless manner and adapted to receive temperature-representative signals from the temperature sensor, pressure-representative signals from the pressure sensor, or both, and wherein the control unit is adapted to calculate the mass flow rate of oxygen passing through the measurement chamber and comprises a data storage unit adapted for writing calibration parameters to and reading said calibration parameters from said data storage unit;

and wherein the control unit is selectively operable in a time-controlled manner, in that the control unit is operated based upon a timing schedule, which is congruent with the descent profile of the aircraft, such that a steeper descent results in a faster change of the required quantity of oxygen.

* * * * *